(12) United States Patent
Ishida et al.

(10) Patent No.: US 8,865,191 B2
(45) Date of Patent: Oct. 21, 2014

(54) LIPID COMPOSITION AND SKIN CARE FORMULATION CONTAINING THE SAME

(75) Inventors: Kenya Ishida, Kanagawa (JP); Kenichiro Shiroyama, Kanagawa (JP)

(73) Assignee: Takasago International Corporation, Kanagawa (JP)

( * ) Notice: Subject to any disclaimer, the term of this patent is extended or adjusted under 35 U.S.C. 154(b) by 1510 days.

(21) Appl. No.: 10/556,183

(22) PCT Filed: Apr. 29, 2004

(86) PCT No.: PCT/IB2004/001487
§ 371 (c)(1),
(2), (4) Date: Nov. 9, 2005

(87) PCT Pub. No.: WO2004/098557
PCT Pub. Date: Nov. 18, 2004

(65) Prior Publication Data
US 2006/0210522 A1   Sep. 21, 2006

(30) Foreign Application Priority Data

May 9, 2003 (JP) ............... P.2003-130948

(51) Int. Cl.
| | | |
|---|---|---|
| A61K 8/42 | (2006.01) | |
| A61K 8/41 | (2006.01) | |
| A61K 8/34 | (2006.01) | |
| A61K 8/68 | (2006.01) | |
| A61Q 5/00 | (2006.01) | |
| A61Q 1/00 | (2006.01) | |
| A61Q 19/10 | (2006.01) | |
| A61Q 19/00 | (2006.01) | |
| A61K 8/02 | (2006.01) | |
| A61Q 5/12 | (2006.01) | |
| A61Q 5/06 | (2006.01) | |
| A61Q 5/02 | (2006.01) | |

(52) U.S. Cl.
CPC ............... *A61Q 19/10* (2013.01); *A61Q 19/00* (2013.01); *A61Q 5/00* (2013.01); *A61K 8/68* (2013.01); *A61Q 5/12* (2013.01); *A61Q 5/06* (2013.01); *A61Q 5/02* (2013.01); *A61K 8/342* (2013.01); *A61K 8/0295* (2013.01)
USPC ........................................ 424/401; 424/70.27

(58) Field of Classification Search
USPC ................................................ 424/401, 70.27
See application file for complete search history.

(56) References Cited

U.S. PATENT DOCUMENTS 5,916,578 A * 6/1999 Kawada et al. ............... 424/401

FOREIGN PATENT DOCUMENTS

| EP | 0 955 038 | 11/1999 |
|---|---|---|
| EP | 1 166 769 | 1/2002 |
| JP | 2001-348319 | 12/2001 |
| JP | 2002-338459 | 11/2002 |
| JP | 2003-055129 | 2/2003 |
| KR | 2002-0025309 | 4/2002 |
| KR | 2002-094478 | 12/2002 |
| WO | WO 98/27958 | 7/1998 |
| WO | WO 01/24767 | 4/2001 |

* cited by examiner

*Primary Examiner* — Sreeni Padmanabhan
*Assistant Examiner* — Sahar Javanmard
(74) *Attorney, Agent, or Firm* — Fitzpatrick, Cella, Harper & Scinto

(57) ABSTRACT

Bioavailability of a ceramide, which is a minimally soluble material of a skin care composition exhibiting an excellent effect is enhanced by combining at least one component selected from ceramides represented by Formula (1):

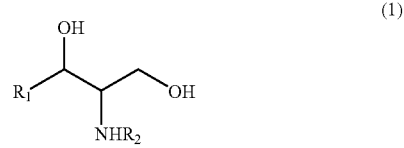

(1)

and at least one component selected from aliphatic alcohol having 12 to 30 carbon atoms.

20 Claims, 1 Drawing Sheet

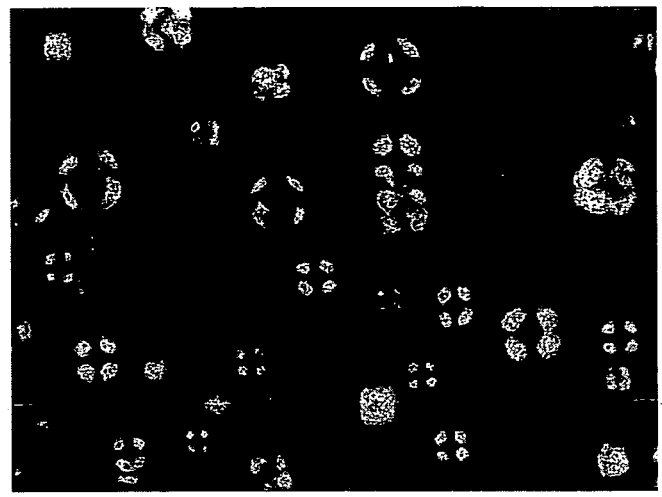

LIPID COMPOSITION AND SKIN CARE FORMULATION CONTAINING THE SAME

BACKGROUND OF THE INVENTION

1. Field of the Invention

The present invention relates to a ceramide-containing lipid composition and a liquid crystal formulation, in which the lipid composition is dispersed stably, and more particularly to a skin care formulation, skin-protecting agent, bath agent and hair care formulation containing the same.

2. Description of the Related Art

A skin plays a very important role as a barrier film which prevents any loss of biologically essential components such as water while serving for a protection from any biological, chemical or physical invasion of external microorganisms, chemicals, ultraviolet light and the like. The part functioning as a barrier film is a horny cell layer whose thickness is about 20 μm and which is located in the outermost layer of the skin and forms a tough barrier film in a structure of the corneocyte stacked as bricks binding to each other via intercellular lipids serving as a mortar. A ceramide is known to play an important role for keeping a skin soft and moist by constructing a lipid barrier as a key component in an inter-corneocyte lipid (see Downing D. T., et al., J. Lipid. Res., 24, 759(1983), Downing D. T., et al., J. Invest. Dermat., 84, 410 (1985)). A ceramide is classified into any of types 1 to 7 based on the structures of a sphingosine base and an acyl side chain as its constituents, and a naturally occurring sphingosine base is known to have a steric structure which is a D-erythro form as an optically active substance.

Recently, a rough skin, dry skin and atopic dermatitis skin are known to have an extremely reduced ceramide content in the inter-corneocyte lipid described above when compared with that in a normal healthy skin, and an attempt is made to improve the roughness of a skin by supplementing a ceramide to a dry or rough skin.

However, any of the ceramides is a hardly soluble compound which has a high crystallinity and a high melting point, and its unique amphiphillic structure leads to an extremely low solubility in almost all oil-soluble/water-soluble cosmetic base material (solvent), resulting in a problem that is difficult in formulating into a product. Thus, when a large amount of ceramide is contained in a product, it undergoes a crystal precipitation, which affects the safety of the product, or becomes less safe especially when combined with a certain oily material for solubilizing the ceramide. Such a problematic tendency becomes more evident when handling a naturally occurring type optically active ceramide, and is desired to be solved.

In a prior attempt (1), a liquid crystal lipid composition consisting of an optically active ceramide and a sterol is proposed to be utilized in a cosmetic product or a skin care formulation (See Japanese Patent Application Laid-Open (JP-A) Nos. 11-12118 and 2001-348320). By using such a liquid crystal composition, an excellent water barrier performance and moistening performance of a naturally occurring type optically active ceramide is realized, but such a liquid crystal lipid has a melting point of 105° C. or more, because of which a special device or a complicated process for formulating a product is required and a further improvement in the stability of the formulated product over a prolonged period is also required.

On the other hand, another prior attempt (2) involves a reduction in the melting point of a ceramide by using a ceramide type 3 having a steric isomeric structure identical to that of a naturally occurring one in combination with a ceramide type 5 and/or a ceramide type 2 (see JP-A 8-225427). In this attempt (2), the ceramide which is available as a steric isomer identical to a naturally occurring one and capable of being in a lamellar structure is only the ceramide type 3, and other naturally occurring type ceramides are taught to be difficult to obtain, and the ceramide types 2 and 5 are employed as racemic mixtures. Thus, the reduction in the melting point is proposed to accomplish by adding the ceramide type 2 which is a mixture of four isomers and the ceramide type 5 which is a mixture of 8 isomers.

While a racemic ceramide is known to have a lower melting point because it is a mixture of isomers, it is also known to have an extremely low effect when compared with a naturally occurring type ceramide, and the reduction in the melting point by adding the racemic ceramide leads to a problem with a reduction also in the efficacy.

SUMMARY OF THE INVENTION

The invention is established in view of the circumstance described above, and its objective is to provide a means for enhancing the bioavailability of a ceramide, which is a hardly soluble material in a skin care formulation. More particularly, an objective of the invention is to provide a composition allowing a ceramide to be formulated easily and exhibiting an excellent effect.

The present inventors made an effort in view of the state of the art described above and finally discovered that a lipid composition consisting of a ceramide and an aliphatic alcohol having 12 to 30 carbon atoms exhibits an excellent compatibility between phases at a temperature of 90° C. or less, and this lipid composition, when combined with a nonionic surfactant, a polyhydric alcohol and an aqueous component, can give a liquid crystal dispersion formulation containing 3% by weight or more of the ceramide and exhibiting excellent stability, safety and skin feel, and also that such a composition can be stably diluted in an oil-in-water product while keeping the liquid crystal state, thus establishing the invention.

Thus, the invention relates to the following lipid compositions, formulations and methods for producing formulations.

1. A lipid composition comprising (1) component (A) and (2) component (B):

(1) the component (A) being at least one component selected from ceramides represented by Formula (1):

(Formula (1))

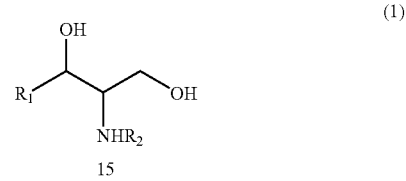

where $R_1$ is a straight hydrocarbon group having 9 to 17 carbon atoms which may have a hydroxyl group and/or a bond(s), $R_2$ is an acyl group having 14 to 30 carbon atoms which may have a hydroxyl group; and (2) the component (B) being at least one component selected from aliphatic alcohol having 12 to 30 carbon atoms, and has an excellent compatibility at 90° C. or less.

2. A lipid composition according to the above-mentioned 1 wherein 95% by mole or more of the component (A) has a D-erythro structure represented by Formula (2):

(Formula (2))

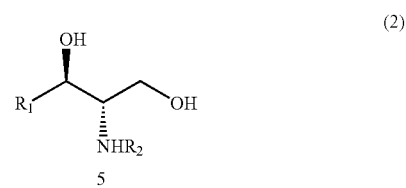

where $R_1$ and $R_2$ are as defined above.

3. A lipid composition according to any one of first and second items wherein the component (A) constitutes 10 to 80% by weight of the entire composition.
4. A lipid composition according to any one of first to third items wherein at least one of the component (A) is (2S,3R)-octadecanoylaminooctadecane-1,3-diol.
5. A lipid composition according to any one of first to fourth items wherein the component (B) is at least one selected from (B-1) cetyl alcohol, stearyl alcohol and behenyl alcohol.
6. A lipid composition according to any one of first to fourth items wherein the component (B) is at least one selected from (B-1) cetyl alcohol, stearyl alcohol and behenyl alcohol and at least one selected from (B-2) cambesterol, stigmasterol, citrosterol and cholesterol.
7. A liquid crystal dispersion formulation comprising a lipid composition according to any one of first to sixth items into which (3) component (c), (4) component (D) and (5) component (E) are incorporated,
   (3) the component (C) being at least one selected from nonionic surfactants,
   (4) the component (D) being at least one selected from polyhydric alcohol, and
   (5) the component (E) being at least one selected from aqueous components,
   in which the liquid crystal formed by the component (A) is dispersed.
8. A liquid crystal dispersion formulation according to seventh item wherein the component (C) is at least one selected from polyglycerin fatty acid esters.
9. A liquid crystal dispersion formulation according to eighth item wherein the polyglycerin fatty acid esters are at least one selected from decaglycerin mono-fatty acid esters.
10. A liquid crystal dispersion formulation according to seventh item wherein the component (D) is at least one selected from 1,3-butylene glycol, glycerin and isoprene glycol.
11. A liquid crystal dispersion formulation according to seventh item wherein the component (E) is water.
12. A liquid crystal dispersion formulation wherein a liquid crystal dispersion formulation according to any one of seventh to eleventh items is in a form of a skin care formulation or hair care formulation.
13. A method for producing a liquid crystal formulation according to any one of seventh to eleventh items comprising 1) solubilizing a lipid composition according to any one of first to sixth items into one phase by warming, 2) diluting the composition with a non-aqueous component containing component (C) and component (D) which have previously been solubilized by warming, and 3) adding component (E) which has previously been warmed followed by cooling.
14. A method for producing an oil-in-water (O/W) type ceramide-containing skin care formulation comprising adding and diluting a liquid crystal dispersion formulation according to the above-mentioned 7 to 11 whose component (A) content is 3% by weight or more.
15. A method for producing an O/W type ceramide-containing hair care formulation comprising adding and diluting a liquid crystal dispersion formulation according to the above-mentioned 7 to 11 whose component (A) content is 3% by weight or more.

BRIEF DESCRIPTION OF THE DRAWING

FIG. 1 is a photograph of the liquid crystal dispersion system of Table 3 exhibiting a morphology in which the Maltese cross image unique to a liquid crystal is dispersed uniformly as observed by a polarizing microscope.

DESCRIPTION OF THE PREFERRED EMBODIMENT

A lipid composition according to the invention contains as an essential component at least one component selected from hardly soluble ceramides as a component (A).

The component (A) employed in the invention is at least one component selected from ceramides represented by Formula (1):
(Formula (1))

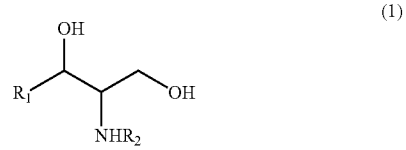

where $R_1$ is a straight hydrocarbon group having 9 to 17 carbon atoms which may have a hydroxyl group and/or double bond(s) and $R_2$ is an acyl group having 14 to 30 carbon atoms, which may have a hydroxyl group.

The component (A) employed in the invention, such as a ceramide represented by Formula (1) is a hardly soluble material. As used herein, a hardly soluble material means a material which is sparingly soluble in water and also difficult to be solubilized together with an oily component under atmospheric pressure at room temperature but precipitates a fine crystal or amorphous solid.

While a ceramide represented by Formula (1) is a known substance and can be obtained from an extract of mammal such as a human or swine skin, bovine brain and erythrocytes, as well as from an extract of a plant such as a soybean and wheat, a synthetic material obtained by a known method (see JP-A 9-235259 and 10-218851) is employed preferably because of its purity.

A compound represented by Formula (1) may for example be, but not limited to, 2-tetradecanoylaminooctadecane-1,3-diol, 2-hexadecanoylaminooctadecane-1,3-diol, 2-octadecanoylaminooctadecane-1,3-diol, 2-eicosanoylaminooctadecane-1,3-diol, 2-oleoylaminooctadecane-1,3-diol, 2-linoleonoylaminooctadecane-1,3-diol, 2-(2-hydroxyhexadecanoyl)aminooctadecane-1,3-diol, 2-(3-hydroxyhexadecanoyl)aminooctadecane-1,3-diol, 2-tetradecanoylaminohexadecane-1,3-diol, 2-hexadecanoylaminohexadecane-1,3-diol, 2-octadecanoylamnohexadecane-1,3-diol, 2-eicosanoylaminohexadecane-1,3-diol, 2-oleoylaminohexadecane-1,3-diol, 2-linoleonoylaminohexadecane-1,3-diol, 2-(2-hydroxyhecadecanoyl)aminohexadecane-1,3-diol, 2-octadecanoylaminooctadecane-1,3,4-triol and the like.

A ceramide in which 95% by mole of the component (A) has an optically active naturally occurring type D-erythro structure represented by Formula (2): (Formula (2))

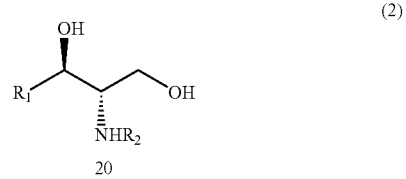

where $R_1$ and $R_2$ are as defined above is preferred especially.

A compound represented by Formula (2) may for example be, but not limited to, (2S,3R)-2-tetradecanoylaminooctadecane-1,3-diol, (2S,3R)-2-hexadecanoylaminooctadecane-1,3-diol, (2S,3R)-2-octadecanoylaminooctadecane-1,3-diol, (2S,3R)-2-nonadecanoylaminooctadecane-1,3-diol, (2S,3R)-2-eicosanoylaminooctadecane-1,3-diol, (2S,3R)-2-oleoylaminooctadecane-1,3-diol, (2S,3R)-2-linoleonoylaminooctadecane-1,3-diol, (2S,3R)-2-(2-hydroxyhexadecanoyl)aminooctadecane-1,3-diol, (2S,3R)-2-(3- hydroxyhexadecanoyl)aminooctadecane-1,3-diol, (2S,3R)-2-tetradecanoylaminohexadecane-1,3-diol, (2S,3R)-2-hexadecanoylaminohexadecane-1,3-diol, (2S,3R)-2-octadecanoylaminohexadecane-1,3-diol, (2S,3R)-2-nonadecanoylaminohexadecane-1,3-diol, (2S,3R)-2-eicosanoylaminohexadecane-1,3-diol, (2S,3R)-2-oleoylaminohexadecane-1,3-diol, (2S,3R)-2-linoleonoylaminohexadecane-1,3-diol, (2S,3R)-2-(2-hydroxyhexadecanoyl)aminohexadecane-1,3-diol, (2S,3S,4R)-2-octadecanoylaminooctadecane-1,3,4-triol and the like.

Among those listed above, (2S,3R)-octadecanoylaminooctadecane-1,3-diol is preferred especially.

In a lipid composition according to the invention, only one component (A) may be employed, or a combination of two or more may also be employed.

A preferred amount of the component (A) in an inventive lipid composition is 10 to 80% by weight based on the entire composition of the lipid composition, more preferably 20 to 50% by weight.

Departing from the range specified above, the compatibility at 90° C. or less with a component (B) will be described below may be lost, or the bioavailability or the liquid crystal dispersibility of the component (A) may be lost.

A lipid composition of the invention contains as an essential component at least one component selected from aliphatic alcohol having 12 to 30 carbon atoms as a component (B).

An aliphatic alcohol having 12 to 30 carbon atoms as a component (B) may for example be a linear aliphatic alcohol (B-1), phytosterol or cholesterol (B-2). Typically, the component (B-1) may for example be an aliphatic alcohol such as lauryl alcohol, myristyl alcohol, cetyl alcohol (cetanol), stearyl alcohol, behenyl alcohol, isostearyl alcohol, oleyl alcohol, oleyl glyceryl ether, farnesol, dihydrofarnesol, geranylgeranyol and the like, with ceryl alcohol, stearyl alcohol and behenyl alcohol being employed preferably. The component (B-2) may for example be a phytosterol or cholesterol such as cambesterol, stigmasterol, citrosterol and the like.

An aliphatic alcohol as a component (B) forms, together with a ceramide as a component (A), a composite matrix as a combination of the states of a liquid crystal, solid solution, solution and the like, whereby exerting an ability of enhancing the bioavailability of a ceramide which is a hardly soluble material as described above.

In an inventive lipid composition, only one component (B) may be employed, or a combination of two or more may also be employed. It is also possible to use one or more component (B-1) in combination with one or more component (B-2) in a suitable ratio. In such a case, a preferred ratio between the component (B-1) and the component (B-2) is within the range from 100:1 to 1:10.

A preferred amount of the component (B) in an inventive lipid composition is 0.5 to 10 times, more preferably 1 to 5 times the total amount of the component (A).

An amount of the component (B) less than 0.5 times may lead to the loss of the compatibility at 90° C. or less, and an amount exceeding 10 times may lead to the loss of the bioavailability of the component (A) or the liquid crystal dispersibility detailed below.

In a lipid composition according to the invention, a component (B-2) is employed preferably as a component for stabilizing the structure of a liquid crystal.

In a method for producing a lipid composition according to the invention, a hardly soluble ceramide component as a component (A) and an aliphatic alcohol as a component (B) are dissolved by heating and then cooling if necessary to mold a waxy or pellet product. While the heating temperature is not limited particularly as long as it allows the component (A) and the component (B) to be compatible into a single phase, it is usually 70 to 150° C., preferably 80 to 110° C.

An inventive lipid composition thus obtained can exhibit a compatibility of the phases at 90° C. or less, and not only eliminates the necessity of a special device or a complicated process for formulating a product but also allows a liquid crystal dispersion formulation whose bioavailability is extremely enhanced to be provided by the following method.

A liquid crystal dispersion formulation of the invention is obtained by incorporating the following components (C), (D) and (E) into an inventive lipid composition described above whereby allowing the liquid crystal formed by a component (A) to be dispersed.

A liquid crystal dispersion formulation of the invention contains as an essential component a lipid composition of the invention described above.

A preferred total amount of a lipid composition of the invention in a liquid crystal dispersion formulation of the invention is 0.5 to 30% by weight, more preferably 1 to 20% by weight, based on the entire composition of the liquid crystal dispersion formulation.

Accordingly, a preferred total amount of the ceramides which are hardly soluble materials as the component (A) is 0.05 to 15% by weight, more preferably 0.2 to 10% by weight, based on the entire composition of the liquid crystal dispersion formulation.

A preferred amount of an aliphatic alcohol as a component (B) is 0.05 to 50% by weight, more preferably 0.1 to 25% by weight, based on the entire composition of the liquid crystal dispersion formulation.

A liquid crystal dispersion formulation of the invention contains at least one component selected from the nonionic surfactants as the component (C).

A liquid crystal dispersion formulation of the invention in a preferred embodiment contains as a preferred component a polyglycerin fatty acid ester in the nonionic surfactant.

A polyglycerin fatty acid ester is preferably has a hydrophile/lipophile balance (HLB) of 10 or more. The polyglycerin group of such a polyglycerin fatty acid ester has a polymerization degree preferably or 5 or more. More preferably the polymerization degree is 8 to 12. The fatty acid residue is preferably one having 12 to 24 carbon atoms, such as lauric acid residue, myristylic acid residue, palmitic acid residue, stearylic acid residue, behenic acid residue, isostearic acid residue, oleic acid residue and the like. The number of such fatty acid residues described above is preferably larger than the number of the free hydroxyl group. Preferably the number of the free hydroxyl group present is 5 to 20 times that of the fatty acid residues. Those especially preferred are decaglycerin monostearate (HLB13.5), pentaglycerin monostearate (HLB11), decaglycerin isostearate (HLB13.5), pentaglycerin monoisostearate (HLB11), decaglycerin monooleate (HLB13) and the like.

Such a component (C) serves as a hydrophilic surfactant in a liquid crystal dispersion formulation of the invention. A polyglycerin fatty acid ester readily forms a liquid crystal structure together with a hardly soluble ceramide component as a component (A) and an aliphatic alcohol as a component (B), and such a liquid crystal structure, once formed at least in a part of a matrix, allows the hardly soluble ceramide component as the component (A) described above to remain on a skin as the matrix that acts transdermal absorption readily.

In a liquid crystal dispersion formulation according to the invention, only one component (C) may be employed, or a combination of two or more may also be employed.

A preferred total amount of the component (C) in a liquid crystal dispersion formulation of the invention is 0.1 to 10% by weight, more preferably 1 to 5% by weight, based on the entire composition of the liquid crystal dispersion formulation.

A liquid crystal dispersion formulation of the invention contains as an essential component at least one component selected from the polyhydric alcohol of the component (D).

A polyhydric alcohol as a component (D) may for example be a polyhydric alcohol such as 1,3-butanediol, dipropylene glycol, glycerin, diglycerin, isoprene glycol, 1,2-pentanediol, 1,2-hexyleneglycol and the like, with 1,3-butylene glycol, glycerin and isoprene glycol being preferred.

Such a component (D) serves as an amphiphillic component in an inventive liquid crystal dispersion formulation. The component (D) readily forms a liquid crystal structure together with a hardly soluble ceramide component as a component (A) and an aliphatic alcohol as a component (B), and such a liquid crystal structure, once formed at least in a part of a matrix, allows the hardly soluble ceramide component as the component (A) described above to remain on a skin as the matrix that acts transdermal absorption readily.

In a lipid crystal dispersion formulation according to the invention, only one component (D) may be employed, or a combination of two or more may also be employed.

A preferred total amount of the component (D) in a liquid crystal dispersion formulation of the invention is 0.1 to 10% by weight, more preferably 1 to 5% by weight, based on the entire composition of the liquid crystal dispersion formulation.

A liquid crystal dispersion formulation of the invention contains as an essential component at least one component selected from the aqueous components as the component (E).

Such an aqueous composition as a component (E) may for example be water, ethanol and the like, with water being preferred.

In a lipid crystal dispersion formulation according to the invention, only one component (E) may be employed, or a combination of two or more may also be employed.

A preferred total amount of the component (E) in a liquid crystal dispersion formulation of the invention is 20 to 90% by weight, more preferably 30 to 80% by weight, based on the entire composition of the liquid crystal dispersion formulation.

A method for producing a liquid crystal dispersion formulation of the invention, involving a process allowing a liquid crystal to be formed easily, may for example be a procedure comprising 1) warming the matrix constituents containing a hardly soluble ceramide component as a component (A) and an aliphatic alcohol as a component (B) to achieve a compatibility of the phases, followed by 2) diluting the matrix with a non-aqueous component, other than the matrix constituent, containing a nonionic surfactant as a component (C) and a polyhydric alcohol as a component (D) which have previously been warmed, followed by 3) combining this diluted material with a previously warmed aqueous components and then cooling.

Other non-aqueous components contained in the diluted material may for example be a nonionic surfactant other than polyglycerin fatty acid esters as well as fragrance and the like.

A nonionic surfactant other than polyglycerin fatty acid esters may for example be a lipophylic nonionic surfactant and a hydrophilic nonionic surfactant.

A lipophylic nonionic surfactant may for example be a sorbitan fatty acid ester such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexanoate, diglycerol sorbitan tetra-2-ethylhexanoate and the like, a glycerin polyglycerin fatty acid ester such a glycerin mono-cottonseed oil fatty acid ester, glycerin mono-erucic acid ester, glycerin sesquioleate, glycerin monostearate, glycerin α,α'-oleate pyroglutamate, glycerin monostearate malate and the like, a propylene glycol fatty acid ester such as polyethylene glycol monostearate as well as a hardened castor oil derivative, glycerin alkyl ether and the like.

A hydrophilic nonionic surfactant may for example be a POE sorbitan fatty acid ester such as POE sorbitan monooleate, POE-sorbitan monostearate, POE-sorbitan monooleate, POE-sorbitan tetraoleate and the like, a POE sorbitol fatty acid ester such as POE-sorbitol monolaurate, POE-sorbitol monooleate, POE-sorbitol pentaoleate, POE-sorbitol monostearate and the like, a POE glycerin fatty acid ester such as POE-glycerin monostearate, POE-glycerin monoisostearate, POE-glycerin triisostearate and the like, a POE fatty acid ester such as POE monooleate, POE distearate and the like, a POE alkyl ether such as POE lauryl ether, POE oleyl ether, POE stearyl ether, POE behenyl ether, POE 2-octyldodecyl ether, POE cholestanol ether and the like, a POE alkylphenyl ether such as POE octylphenyl ether, POE nonylphenyl ether, POE dinonylphenyl ether and the like, a pluaronic type material such as Pluronic, a POE.POP alkyl ether such as POE.POP cetyl ether, POE.POP 2-decyltetradecyl ether, POE.POP monobutyl ether, POE.POP hydrogenated lanolin, POE.POP glycerin ether and the like, a tetra POE.tetra POP ethlene diamine condensation product such as tetronic, a POE castor oil hardened castor oil derivative such as POE castor oil, POE hardened castor oil, POE hardened castor oil monoisostearate, POE hardened castor oil triisostearate, POE hardened castor oil monopyroglutamate monoisostearate, POE hardened castor oil maleate and the like, a POE beeswax lanolin derivative such as POE sorbitol beeswax, an alkanolamide such as palm oil fatty acid diethanolamide, lauric acid monoethanolamide, fatty acid isopropanolamide and the like, as well as a POE propylene glycol fatty acid ester, POE alkylamine, POE fatty acid amide, sucrose fatty acid ester, POE nonylphenyl formaldehyde condensate, alkylethoxydimethylamine oxide, trioleylphosphoric acid and the like.

Among the above-mentioned surfactants other than the polyglyerin fatty acid esters, a hydrophilic nonionic surfactant is employed preferably, with a surfactant having no polyoxyethylene backbone being more preferred. Typically, a sucrose fatty acid ester is preferred, including sucrose stearate (HLB: about 11, 15, 19), sucrose palmitate (HLB: about 16), sucrose myristate (HLB: about 16), sucrose laurate (HLB: about 16), sucrose oleate (HLB: about 15), sucrose distearate (HLB: about 6, 8) and the like.

A preferred amount of such a sucrose fatty acid ester to be added in total is 0.05 to 10% by weight, more preferably 0.1 to 5% by weight based on the entire liquid crystal dispersion formulation.

A liquid crystal dispersion formulation of the invention may optionally contain any other components employed usually in a skin care formulation such as a cosmetic formulation or dermal pharmaceutical formulation discretely in its liquid crystal-forming component phase, non-aqueous component phase excluding the liquid crystal-forming components and water phase as long as the benefits of the invention discussed above is not affected adversely.

Such an optional component may for example be an ionic surfactant, such as anionic surfactant including a soap base, a fatty acid soap such as sodium laurate, sodium palmitate and the like, a higher alkyl sulfate salt such as sodium lauryl sulfate, potassium lauryl sulfate and the like, an alkyl ether sulfate salt such as triethanolamine POE (polyoxyethylene) lauryl sulfate, sodium POE lauryl sulfate and the like, a higher fatty acid amide sulfonate such as sodium N-myristoyl-N-methyltaurin, sodium palm oil fatty acid methyltaurid, sodium laurylmethyltaurid and the like, a phosphate salt such as sodium POE oleyl ether phosphate, POE stearyl ether phosphoric acid and the like, a sulfosuccinate such as sodium di-2-ethylhexylsulfosuccinate, sodium monolauroylmonoethanolamide polyoxyethylene sulfosuccinate, sodium laurylpolypropylene glycolsulfosuccinate and the like, an alkylbenzene sulfonate such as sodium linear dodecylbenzene sulfonate, triethanolamine linear dodecylbenzene sulfonate, linear dodecylbenzene sulfonic acid and the like, an N-acylglutamate such as monosodium N-lauroylgultamate, disodium N-stearoylglutamate, monosodium N-myristoyl-L-glutamate and the like, a higher fatty acid ester sulfate salt such as sodium hardened palm oil fatty acid glycerin sulfate, a sulfated oil such as turkey red oil, as well as a POE alkyl ether caboxylic acid, POE alkylallyl ether carboxylic acid, α-olefin sulfonate, higher fatty acid ester sulfonate, secondary alcohol sulfate salt, higher fatty acid alkylolamide sulfate salt, sodium succinate lauroyl monoethanolamide, ditriethanolamine N-palmitoylaspartate, sodium caseinate and the like.

A cationic surfactant may for example be an alkyltrimethylammonium salt such as stearyl trimethylammonium chloride, lauryl trimethylammonium chloride and the like, an alkylpyridinium salt such as a dialkyldimethylammonium salt such a distearyl dimethylammonium chloride, poly(N,N'-dimethyl-3,5-methylenepiperidinium) chloride and cetylpyridinium chloride, an alkyl quaternary ammonium salt, alkyldimethylbenzylammonium salt, alkylisoquinolinium salt, dialkylmorpholinium salt, POE alkylamine, alkylamine salt, polyamine fatty acid derivative, amylalcohol fatty acid derivative, benzalkonium chloride, benzethonium cloride and the like.

An amphoteric surfactant may for example be an imidazoline-based amphoteric surfactant such as sodium 2-undecyl-N,N,N-(hydroxyethylcarboxymethyl)-2-imidazoline, 2-cocoyl-2-imidazolinium hydroxide-1-carboxyethyloxydisodium salt and the like, and a betaine-based surfactant such as betain 2-heptadecyl-N-carboxymethl-N-hydroxyethylimidazolinium, betain lauryldimethylamonoacetate, alkylbetaine, amidobetaine, sulfobetaine and the like.

Such an optional component, other than the ionic surfactants exemplified above, may for example be a hydrocarbon such as squalane, liquid paraffin, light liquid isoparaffin, heavy liquid isoparaffin, microcrystaline wax, solid paraffin and the like, a silicone such as dimethicone, phemethicone, cyclomethicone, amodimethicone, polyether-modified silicone and the like, an ester such as jojoba oil, carnauba wax, Japan tallow, beeswax, spermaceti, octyldodecyl oleate, isopropyl myristate, neopentylglycol diisostearate, diisostearate malate and the like, a fatty acid such as stearic acid, lauric acid, myristic acid, palmitic acid, isostearic acid, isopalmitic acid, behenic acid, oleic acid and the like, a triglyceride such as castor oil, palm oil, hydrogenated palm oil, camellia oil, wheat germ oil, isostearic acid triglyceride, isooctanoic acid triglyceride, olive oil and the like, a polyhydric alcohol such as 1,3-butanediol, glycerin, diglycerin, dipropylene glycol, polyethylene glycol, 1,2-pentanediol, 1,2-hexylene glycol, isoprene glycol and the like, an organic powder such as crystalline cellulose, crosslinked methylpolysiloxane, polyethylene powder, acrylic resin powder and the like, an optionally coated powder such as talc, mica, sericite, magnesium carbonate, calcium carbonate, titanium dioxide, iron oxide, prussian blue, ultramarine, titanium mica, titanium sericite, silica and the like, a thickening agent such as acrylic acid/methacrylic acid alkyl copolymer and/or its salt, carboxyvinyl polymer and/or its salt, xanthane gum and hydroxypropyl cellulose, an active ingredient such as a vitamin including retiol, retinoic acid, tocopherol, riboflavin, pyridoxine, ascorbic acid, ascorbate phosphate salt and the like or a steroid including estradiol, ethynylestradiol, estriol and the like, a preservative such as paraben, hibitane gluconate, benzalkonium chloride, phenoxyethanol and the like, an UV absorber such as dimethylaminobenzoate, cinnamic ester, benzophenone and the like. A liquid crystal dispersion formulation of the invention may be applied also to a formulation other than cosmetic or skin care pharmaceutical formulations.

A liquid crystal dispersion formulation containing 3% by weight or more of a ceramide thus obtained may directly be used as a skin care formulation, or may be diluted into various products by ordinary procedures. It is preferable generally to formulate into a lotion, cream, gel, emulsion and the like.

A liquid crystal dispersion formulation of the invention thus obtained contains a hardly soluble ceramide in an amount of 3% by weight or more, allows the ceramide to be dissolved readily and also enhances the bioavailability, and is being capable of diluted into an oil-in-water product while maintaining its liquid crystalline state, resulting in an extremely widened application to the formulations.

EXAMPLES

The invention is further detailed in the following Examples and Experiments, which are not intended to restrict the invention. Unless otherwise specified, any of the optically active ceramides described below was synthesized and analyzed in accordance with JP-A 9-235259 and JP-A 10-218851 and those having both 95% or more chemical and optical purities of the D-erythro(2S,3R) form were employed.

Examples 1 to 7 and Comparative Examples 1 to 4

Experiment 1

Compatibility Test (1)

The melting point of (2S,3R)-2-Octadecanoylaminooctadecane-1,3-diol having both 95% or higher chemical and optical purities (optically active ceramide 2):each test sample=50:50 (mass ratio) was measured in accordance with Method 2 of the Melting Point Test under the Cosmetic Material Standard. The results are shown in Table 1. In this table, x designates the sample requiring 100° C. or more. As evident from Table 1, the ceramide is highly compatible with a higher alcohol and a higher fatty acid.

TABLE 1

|  | Test Sample | Melting Point |
| --- | --- | --- |
| Example 1 | Cetanol | 83° C. |
| Example 2 | Behenyl alcohol | 86° C. |
| Example 3 | Octyldodecanol | 88° C. |
| Example 4 | Oleyl glyceryl ether | 90° C. |
| Example 5 | Oleyl alcohol | 88° C. |
| Example 6 | Isostearyl alcohol | 87° C. |
| Example 7 | Dihydrifarnesol | 85° C. |
| Reference 1 | Isostearic acid | 86° C. |
| Reference 2 | Stearic acid | 87° C. |
| Comparative Example 1 | Squalane | x |
| Comparative Example 2 | Liquid paraffin | x |

TABLE 1-continued

| | Test Sample | Melting Point |
|---|---|---|
| Comparative Example 3 | Glyceryl trioctanoate | x |
| Comparative Example 4 | Jojoba oil | x |

Examples 8 to 14

Experiment 2

Compatibility Test (2)

The melting point of optically active ceramide 2:each test sample:cholesterol=40:30:30 (mass ratio) was measured in accordance with Method 2 of the Melting Point Test under the Cosmetic Material Standard. The results are shown in Table 2.

TABLE 2

| | Test Sample | Melting Point |
|---|---|---|
| Example 8 | Cetanol | 80° C. |
| Example 9 | Behenyl alcohol | 87° C. |
| Example 10 | Octyldodecanol | 84° C. |
| Example 11 | Oleyl glyceryl ether | 85° C. |
| Example 12 | Oleyl alcohol | 83° C. |
| Example 13 | Isostearic acid | 80° C. |
| Example 14 | Stearic acid | 82° C. |

Examples 15 to 19 and Comparatives Examples 5 and 6

Experiment 3

Preparation of Emulsion Formulation

The lipid composition (i) obtained in the compatibility test (2) (Examples 8 to 14) was used to prepare the skin care formulations of the invention having the compositions shown below. Thus, each of the component (i), a component (ii) and a component (iii) were kept at 95° C., and ensured for its homogeneity. Then the component (ii) was added to the component (i) for dilution, and to this mixture the component (iii) was added in portions with stirring, and the mixture was cooled with stirring to obtain an inventive skin care formulation 1.

| Skin Care Formulation 1 | | |
|---|---|---|
| Component (i) | | |
| Lipid composition | 10 | Parts by weight |
| Component (ii) | | |
| Decaglycerin monostearate | 5 | Parts by weight |
| 1,3-Butylene glycol | 10 | Parts by weight |
| Glycerin | 5 | Parts by weight |
| Phenoxyethanol | 1 | Part by weight |
| Component (iii) | | |
| Water | 69 | Parts by weight |

The formulation thus obtained was observed by a polarizing microscope. The results are shown in Table 3.
In Table 3, the liquid crystal dispersion system means a morphology in which the Maltese cross unique to a liquid crystal is dispersed uniformly as shown in the photograph of FIG. 1.

TABLE 3

| | Sample | System morphology |
|---|---|---|
| Example 15 | Cetanol | Liquid crystal dispersion system |
| Example 16 | Behenyl alcohol | Liquid crystal dispersion system |
| Example 17 | Octyl dodecanol | Liquid crystal dispersion system |
| Example 18 | Oleyl glyceryl ether | Liquid crystal dispersion system |
| Example 19 | Oleyl alcohol | Liquid crystal dispersion system |
| Comparative Example 5 | Isostearic acid | Amorphous |
| Comparative Example 6 | Staric acid | Amorphous |

It was revealed that any of the formulations of Examples 15 to 19 was in a state in which microparticles having liquid crystal structures were dispersed uniformly. It was also revealed that a homogeneous component (i) formed a liquid crystal, and that the state in which the component (i) is diluted with the component (ii) is a multi-phase state allowing the liquid crystal and the vehicle to coexist. While no crystal was observed in the formulation using a long chain fatty acid in Comparative 5 or 6, no liquid crystalline state was identified.

Comparative Example 7

A formulation was made by a different method using the same composition used in Example 15. Thus, the component (i) was dissolved uniformly at 95° C., and to this then the components (ii) and (iii) which had been dissolved uniformly at 95° C. were added in portions, and the mixture was cooled with stirring to obtain an emulsion skin care formulation 2.
While no crystal was observed in the formulation obtained in Comparative Example 7, no liquid crystalline state was identified.

Experiment 4

Skin-Feel Test

Using the skin care formulations of Example 5 and Comparative Example 7, the skin feel was compared by experienced panelists (n=10). The skin feel was evaluated with regard to spreadability on the skin the moistness after application and the smoothness after application, and judged as score 5: very good, score 4: good, score 3: moderate, score 2: slightly poor and score 1: poor, and the mean of the scores was calculated.
The results are shown in Table 4. As evident from this, the inventive skin care formulation exhibited an excellent skin feel. This excellent skin feel is attributable to the dispersion of the ceramide as a liquid crystalline state.

TABLE 4

| Evaluation item | Example 15 Skin care formulation 1) | Comparative 7 (Skin care formulation 2) |
|---|---|---|
| Spreadability on skin | 4.5 | 3.8 |
| Moistness after application | 4.2 | 3.0 |
| Smoothness after application | 4.0 | 2.5 |

Experiment 5

Stability Test

The skin care formulations of Example 1 and Comparative 3 were examined for the stability over a time period.

After preparing the formulation, the formulation was allowed to stand at room temperature for 1 month, 40° C. for 1 month and 5° C. for 1 month, and then examined for the appearance by visual observation and also for the system condition by a microscope. The results are shown in Table 5.

As evident from Table 5, the liquid crystal dispersion formulation prepared in Example 15 had an excellent stability.

TABLE 5

| Evaluation item | Example 15 (Skin care formulation 1) | Comparative Example 7 (Skin care formulation 2) |
|---|---|---|
| Appearance | Uniform | Precipitation |
| System condition | Liquid crystal dispersion | Partly crystallized |

Examples 20 to 26 and Comparative Example 8

According to the method for producing the skin care formulation 1 but changing the component (i), an investigation was made to examine whether a liquid crystal dispersion system is formed or not. The results are shown in Table 6. The racemic ceramide was obtained by converting a racemic sphinganine obtained by the method by D. Shapiro., et al., (J. Am. Chem. Soc., 80, 2170(1958)) into its stearoyl form.

| Component (i) | |
|---|---|
| Wheat germ-derived phytosterol mixture | 2 Parts by weight |
| Cetanol | 5 Parts by weight |
| Component shown in Table 6 | 3 Parts by weight |
| δ-Tocopherol | 0.1 Parts by weight |
| Component (ii) | |
| Decaglycerin monostearate | 5 Parts by weight |
| Sucrose palmitate | 1 Part by weight |
| Isoprene glycol | 10 Parts by weight |
| Glycerin | 5 Parts by weight |
| Phenoxyethanol | 1 Part by weight |
| Component (iii) | |
| Water | 67.9 Parts by weight |

TABLE 6

| Example | Sample name | Liquid crystal backbone component | System morphology |
|---|---|---|---|
| Example 20 | Skin care formulation 3 | Ceramide 5 | Liquid crystal dispersion system |
| Example 21 | Skin care formulation 4 | Ceramide 1 | Liquid crystal dispersion system |
| Example 22 | Skin care formulation 5 | Ceramide 2/Ceramide 5 = 1/1 (weight ratio) | Liquid crystal dispersion system |
| Example 23 | Skin care formulation 6 | Ceramide 2/Ceramide 5 = 9/1 (weight ratio) | Liquid crystal dispersion system |
| Example 24 | Skin care formulation 7 | Ceramide 2/sphinganine = 9/1 (weight ratio) | Liquid crystal dispersion system |
| Example 25 | Skin care formulation 8 | Ceramide 2/acetylsphinganine = 9/1 (weight ratio) | Liquid crystal dispersion system |
| Example 26 | Skin care formulation 9 | Ceramide 2/Ceramide 5/sphinganine = 7/2/1 (weight ratio) | Liquid crystal dispersion system |
| Comparative Example 8 | Skin care formulation 8 | Racemic ceramide 2 | Partial liquid crystal dispersion system |

As a result, any of the optically active ceramide, sphinganine derivative and their mixture were proven to be capable of forming a liquid crystal dispersion system, while the racemic ceramide was proven to be difficult to form a stable liquid crystal dispersion system although a liquid crystal was present partially.

Example 27

According to a standard method, 97.5 g of the following lotion was prepared and combined with stirring at room temperature with 2.5 g of the external formulation of Example 17 to obtain 100 g of a lotion containing the ceramide 2 at 0.1%.

| Concentrated glycerin | 3.00 |
|---|---|
| 1,3-Butylene glycol | 5.00 |
| Ester p-Hydroxybenzoate | 0.20 |
| Fragrance | 0.01 |
| Purified water to | 97.50 |

Example 28

According to a standard method, 75.0 g of the following cosmetic lotion was prepared and combined with stirring at room temperature with 25 g of the external formulation of Example 15 to obtain 100 g of a cosmetic lotion containing the ceramide 2 at 0.1%.

| Hydroxyethyl cellulose | 0.50 |
|---|---|
| Concentrated glycerin | 5.00 |
| 1,3-Butylene glycol | 5.00 |
| Ester p-Hydroxybenzoate | 0.20 |
| Fragrance | 0.01 |
| Ceramide composition of Example 2 | 25.00 |
| Purified water to | 75.00 |

Example 29

According to a standard method, 90.0 g of the following emollient cream was prepared and combined with stirring at room temperature with 10.0 g of the external formulation of Example 22 to obtain 100 g of an emollient cream containing the ceramide 2/ceramide 5=1/1 (weight ratio) at 0.3%.

| Hardened oil | 6.00 |
|---|---|
| Stearic acid | 3.00 |
| Cetanol | 4.00 |
| Squalane | 2.00 |
| Neopentyl glycol dicaprate | 8.00 |

| | |
|---|---|
| Polyoxyethylene sorbitan monostearate (20E.O.) | 4.00 |
| Lipophylic glycerin monostearate | 2.30 |
| Sodium stearoyl-N-methyltaurin | 1.70 |
| 1,3-Butylene glycol | 7.00 |
| Concentrated glycerin | 3.00 |
| Ester p-Hydroxybenzoate | 0.25 |
| Fragrance | 0.05 |
| Purified water to | 90.00 |

Example 30

According to a standard method, 95.0 g of the following emollient milk was prepared and combined with stirring at room temperature with 5.0 g of the external formulation of Example 22 to obtain 100 g of an emollient milk containing the ceramide 2/ceramide 5=9/1 (weight ratio) at 0.15%.

| | |
|---|---|
| Stearic acid | 1.00 |
| Cholesteryl isostearate | 2.00 |
| Jojoba oil | 4.00 |
| Squalane | 8.00 |
| Sorbitan sesquioleate | 0.80 |
| Polyoxyethylene sorbitan monostearate (20E.O.) | 1.20 |
| 1,3-Butylene glycol | 5.00 |
| Ester p-Hydroxybenzoate | 0.25 |
| L-Arginine | 0.40 |
| Carboxyvinyl polymer | 0.20 |
| Fragrance | 0.05 |
| Purified water to | 95.00 |

Example 31

According to a standard method, 97.5 g of the following conditioning shampoo was prepared and combined with stirring at room temperature with 2.5 g of the external formulation of Example 15 to obtain 100 g of a conditioning shampoo containing the ceramide 2 at 0.1%.

| | |
|---|---|
| Sodium polyoxyethylene lauryl ether sulfate | 14.00 |
| Amidopropylbetaine laurate | 4.00 |
| Palm oil fatty acid diethanolamide | 3.00 |
| Cationic cellulose | 0.50 |
| Ethylene glycol distearate | 1.00 |
| Ester p-Hydroxybenzoate | 0.25 |
| Citric acid | qs |
| Fragrance | 0.50 |
| Purified water to | 97.50 |

Example 32

According to a standard method, 95.0 g of the following hair rinse was prepared and combined with stirring at room temperature with 5.0 g of the external formulation of Example 15 to obtain 100 g of a hair rinse containing the ceramide 2 at 0.2%.

| | |
|---|---|
| Stearyltrimethylammonium chloride | 1.00 |
| Cetanol | 3.00 |
| Methylpolysiloxane | 1.00 |
| Polyoxyethylene stearyl ether | 1.00 |
| Propylene glycol | 5.00 |
| Ester p-Hydroxybenzoate | 0.25 |
| Sodium hydroxide | qs |
| Citric acid | qs |
| Fragrance | 0.50 |
| Purified water to | 95.00 |

Example 33

According to a standard method, 90.0 g of the following hair conditioner was prepared and combined with stirring at room temperature with 10.0 g of the external formulation of Example 22 to obtain 100 g of a hair conditioner containing the ceramide 2/ceramide 5=9/1 (weight ratio) at 0.3%.

| | |
|---|---|
| Stearyltrimethylammonium chloride | 0.50 |
| Ditearyldimethylammonium chloride | 1.50 |
| Jojoba oil | 2.50 |
| Cetanol | 4.50 |
| Liquid lanolin | 2.00 |
| Polyoxyethylene stearyl ether | 1.50 |
| Concentrated glycerin | 7.00 |
| Ester p-Hydroxybenzoate | 0.25 |
| Sodium hydroxide | qs |
| Citric acid | qs |
| Fragrance | 0.50 |
| Purified water to | 90.00 |

Example 34

According to a standard method, 97.5 g of the following hair tonic was prepared and combined with stirring at room temperature with 2.5 g of the external formulation of Example 15 to obtain 100 g of a hair tonic containing the ceramide 2 at 0.1%.

| | |
|---|---|
| Japanese green gentian extract | 2.00 |
| L-Menthol | 0.10 |
| Hinokithiol | 0.01 |
| Fragrance | 0.10 |
| Ester p-Hydroxybenzoate | 0.20 |
| Polyoxyethylene hardened castor oil | 0.50 |
| Purified water to | 97.50 |

Example 35

According to a standard method, 95.0 g of the following hair blow lotion was prepared and combined with stirring at room temperature with 5.0 g of the external formulation of Example 22 to obtain 100 g of a hair blow lotion containing the ceramide 2/ceramide 5=9/1 (weight ratio) at 0.15%.

| | |
|---|---|
| Polyoxyethylene polyoxypropylene butyl ether | 0.50 |
| Polyvinyl pyrrolidone | 2.50 |
| Stearyltrimethylammonium chloride | 4.50 |
| Polyether-modified silicone | 2.00 |
| p-Oxybenzoate | 0.20 |
| Citric acid | qs |
| Fragrance | 0.10 |
| Purified water to | 95.00 |

Example 36

According to a standard method, 95.0 g of the following bath gel was prepared and combined with stirring at room temperature with 5.0 g of the external formulation of Example 22 to obtain 100 g of a bath gel containing the ceramide 2/ceramide 5=9/1 (weight ratio) at 0.15%.

| | |
|---|---|
| Dipropylene glycol | 50.00 |
| 1,3-Butylene glycol | 10.00 |
| Ester p-Hydroxybenzoate | 0.20 |
| Fragrance | 1.00 |
| Purified water to | 95.00 |

As detailed above, the invention provides a means for enhancing the bioavailability of a hardly soluble ceramide which is a lipid composition consisting of a ceramide and an aliphatic alcohol having 12 to 30 carbon atoms and exhibits an excellent compatibility at 90° C. or less and also allows a formulation to be prepared easily while also allowing a liquid crystal dispersion formulation containing the inventive lipid composition having excellent stability, safety and skin feel to be prepared. It also allows the liquid crystal dispersion formulation to be diluted stably in an oil-in-water product while keeping the liquid crystalline state, resulting in an extremely widened application to the source materials for cosmetic or pharmaceutical products.

What is claimed is:

1. A method for producing a lipid composition suitable for use in cosmetics consisting of components (A) and (B), and optionally at least one member selected from the group consisting of nonionic surfactant, polyhydric alcohol, water and ethanol, wherein the total amount of component (B) is 0.5 to 10 times by weight the total amount of component (A) and the lipid composition has an excellent compatibility at 90° C. or less, the method comprising heating and melting said components (A) and (B) at 80 to 110° C.,
    said component (A) being at least one ceramide represented by Formula (1):

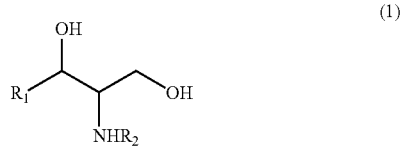

(1)

where $R_1$ is a straight hydrocarbon group having 9 to 17 carbon atoms which may have a hydroxyl group and/or a double bonds, $R_2$ is an acyl group having 14 to 30 carbon atoms which may have a hydroxyl group; and
    said component (B) being at least one member (B-1) selected from the group consisting of cetyl alcohol, stearyl alcohol and behenyl alcohol, and at least one member (B-2) selected from cambesterol, stigmasterol, citrosterol and cholesterol.

2. The method according to claim 1, wherein 95% by mole or more of the component (A) has a D-erythro structure represented by Formula (2):

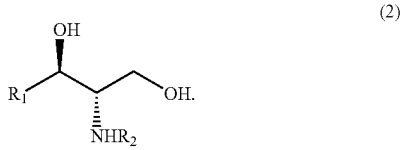

(2)

3. The method according to claim 1, wherein said component (A) constitutes 10 to 80% by weight of the entire composition.

4. The method according to claim 3, wherein at least a portion of component (A) is (2S,3R)-octadecanoylaminooctadecane-1,3-diol.

5. A method for producing a liquid crystal formulation, comprising:
    1) producing a lipid composition according to claim 3 and solubilizing said lipid composition into one phase by warming,
    2) diluting said composition with a non-aqueous component containing at least one nonionic surfactant and at least one polyhydric alcohol which are solubilized by warming, and
    3) adding at least one warmed aqueous component,
    4) followed by cooling.

6. A method for producing a skin or hair care formulation, comprising producing an oil-in-water ceramide-containing emulsion from the liquid crystal formulation according to claim 5, wherein the content of component (A) in said emulsion is 3% by weight or more.

7. The method according to claim 2, wherein said component (A) constitutes 10 to 80% by weight of the entire composition.

8. The method according to claim 7, wherein at least a portion of component (A) is (2S,3R)-octadecanoylaminooctadecane-1,3-diol.

9. A method for producing a liquid crystal formulation, comprising:
    1) producing a lipid composition according to claim 7 and solubilizing said lipid composition into one phase by warming,
    2) diluting said composition with a non-aqueous component containing at least one nonionic surfactant and at least one polyhydric alcohol which are solubilized by warming, and
    3) adding at least one warmed aqueous component,
    4) followed by cooling.

10. A method for producing a skin or hair care formulation, comprising producing an oil-in-water ceramide-containing emulsion from the liquid crystal formulation according to claim 9, wherein the content of component (A) is 3% by weight or more.

11. The method according to claim 1, wherein said lipid composition contains said nonionic surfactant.

12. The method according to claim 11, wherein the nonionic surfactant is a polyglycerin fatty acid ester.

13. The method according to claim 12, wherein the polyglycerin fatty acid ester has an HLB of at least 10 and a polymerization degree of at least 5, said nonionic surfactant being contained at 0.1 to 10% by weight of said lipid composition.

14. The method according to claim 13, wherein the polyglycerin fatty acid ester has an HLB of 8-12, and a fatty acid residue with 12 to 24 carbon atoms, said nonionic surfactant being contained at 1 to 5% by weight of said lipid composition.

15. The method according to claim 1, wherein said lipid composition contains said polyhydric alcohol, said polyhydric alcohol being contained at 0.1 to 10% by weight of said lipid composition.

16. The method according to claim 15, wherein said polyhydric alcohol is contained at 1 to 5% by weight of said lipid composition.

17. The method according to claim 11, wherein said lipid composition is aqueous.

18. The method according to claim 17, wherein said lipid composition contains ethanol.

19. The method according to claim 15, wherein said lipid composition is aqueous.

20. The method according to claim 19, wherein said lipid composition contains ethanol.

* * * * *

UNITED STATES PATENT AND TRADEMARK OFFICE
CERTIFICATE OF CORRECTION

PATENT NO. : 8,865,191 B2
APPLICATION NO. : 10/556183
DATED : October 21, 2014
INVENTOR(S) : Kenya Ishida et al.

It is certified that error appears in the above-identified patent and that said Letters Patent is hereby corrected as shown below:

In The Specification

COLUMN 1:

Line 13, "A skin" should read --Skin--;
Line 15, "a" should be deleted;
Line 20, "a" should be deleted and "A ceramide" should read --Ceramide--;
Line 21, "a" (first occurrence) should be deleted;
Line 30, "a" should be deleted;
Line 33, "a" should be deleted;
Line 34, "a" should read --the--;
Line 35, "a" should be deleted;
Line 36, "any of the ceramides is a hardly" should read --ceramides are poorly--;
Line 37, "pound which has" should read --pounds having--;
Line 38, "its" should read --their--;
Line 40, "material" should read --materials--; and
Line 41, "in formulating" should read --to formulate--.

COLUMN 2:

Line 1, "taught to be" should be deleted;
Line 46, "15" should be deleted; and
Line 65, "5" should be deleted.

COLUMN 4:

Line 55, "20" should be deleted.

Signed and Sealed this
Fourteenth Day of April, 2015

Michelle K. Lee
*Director of the United States Patent and Trademark Office*

CERTIFICATE OF CORRECTION (continued)
U.S. Pat. No. 8,865,191 B2

COLUMN 6:

Line 13, "whereby" should read --thereby--;
    Line 39, "is" should be deleted;
    Line 49, "group." should read --groups.--;
    Line 50, "group" should read --groups--;
    Line 63, "a" should read --the--;
    Line 64, "acts transdermal absorption readily" should read --readily absorbs transdermally--; and
    Line 65, "lipid" should read --liquid--.

COLUMN 7:

Line 22, "acts transdermal absorption readily" should read --readily absorbs transdermally--;
    Line 23, "lipid" should read --liquid--; and
    Line 37, "lipid" should read --liquid--.

COLUMN 8:

Line 63, "is" should read --are--.

COLUMN 9:

Line 30, "such a" should read --,--.

COLUMN 10:

Line 7, "retiol," should read --retinol,--; and
    Line 25, "being capable of diluted" should read --capable of being diluted--.

COLUMN 12:

Line 10, "Staric acid" should read --Stearic acid--.

In The Claims

COLUMN 17:

Line 46, "bonds," should read --bond(s),--.